United States Patent
Grözinger et al.

(10) Patent No.: US 7,587,024 B2
(45) Date of Patent: Sep. 8, 2009

(54) PARTICLE BEAM IRRADIATION SYSTEM

(75) Inventors: Sven Oliver Grözinger, Herzogenaurach (DE); Michael Farley Moyers, Colton, CA (US)

(73) Assignee: Siemens Aktiengesellschaft, Munich (DE)

( * ) Notice: Subject to any disclaimer, the term of this patent is extended or adjusted under 35 U.S.C. 154(b) by 242 days.

(21) Appl. No.: 11/514,630

(22) Filed: Sep. 1, 2006

(65) Prior Publication Data

US 2008/0056434 A1 Mar. 6, 2008

(51) Int. Cl.
*A61N 5/10* (2006.01)
*G21K 5/00* (2006.01)
*G01N 23/04* (2006.01)

(52) U.S. Cl. .............................. 378/65; 378/62; 378/63; 378/64

(58) Field of Classification Search ............... 378/62, 378/63, 147, 150, 151, 204, 205, 206; 606/4, 606/10, 13, 17; 600/160, 249, 452, 427; D24/137, 138, 150, 180, 160, 172; 362/572; 250/492.1, 493.1
See application file for complete search history.

(56) References Cited

U.S. PATENT DOCUMENTS

| | | | |
|---|---|---|---|
| 4,726,046 A | | 2/1988 | Nunan |
| 5,745,545 A | * | 4/1998 | Hughes .......................... 378/65 |
| 5,792,147 A | * | 8/1998 | Evans et al. .................. 606/130 |
| 5,823,192 A | * | 10/1998 | Kalend et al. ................ 128/845 |
| 2002/0065461 A1 | * | 5/2002 | Cosman ....................... 600/426 |
| 2006/0017022 A1 | * | 1/2006 | Rigney et al. ............. 250/497.1 |

OTHER PUBLICATIONS

Daftari, et al, Design, development, and performance of an adapter for simulation of ocular melanoma patients in supine position for proton beam therapy, Jun. 2003, American Institute of Physics, Review of Scientific Instruments, vol. 74, No. 6, pp. 3093-3097.*
G.A.P. Cirrone, et al., "A 62-MeV Proton Beam for the Treatment of Ocular Melanoma at Laboratori Nazionali del Dud-INFN", IEEE Transactions on Nuclear Science IEEE USA, vol. 51, No. 3, Jun. 2004, pp. 860-865, XP007906759, ISSN: 0018-9499.
Dr. Giacomo Cuttone, et al., Wsperienze di Proton Terapia all'INFN—LNS di Cantania: II primo anno di trattamenti, Prima conferenza AIRO, Mar. 21, 2003, p. 1-42, XP007906741; 2003; ES. http://www.1ns.infn.it/CATANA/CATANA/documents.ht; retrieved on Jan. 8, 2009—Clips; XP007906739; 2009.

* cited by examiner

*Primary Examiner*—Edward J Glick
*Assistant Examiner*—Anastasia Midkiff
(74) *Attorney, Agent, or Firm*—Brinks Hofer Gilson & Lione

(57) ABSTRACT

A system for treating an ocular tumor having a cone, a collimator, a light source and a camera is disclosed. The cone includes a cone input and a cone output and is capable of being mounted and un-mounted to a treatment nozzle. The cone input receives radiation from the treatment nozzle for the treatment of the ocular tumor. The collimator is coupled to the cone output and configured to collimate radiation received by the cone output. This collimated radiation is directed to the patient having the ocular tumor. The light source coupled to the cone. The light source is configured to provide a focusing point of the eye of the patient. A camera coupled to the cone monitors the position of the eye of the patient.

24 Claims, 3 Drawing Sheets

PARTICLE BEAM IRRADIATION SYSTEM

BACKGROUND

I. Technical Field

The present embodiments generally relate to particle beam irradiation systems for treating ocular tumors.

II. Background

Particle therapy systems for the treatment of ocular tumors use dedicated beam lines for the irradiation of the ocular tumor. Irregularly shaped tumors with awkward configurations near critical structures are well suited for proton beam therapy. Protons have a physical advantage over gamma rays and x-rays when it comes to sparing normal tissues. Protons deposit most of their radiation energy in what is known as the Bragg peak, which occurs at the point of greatest penetration of the protons in tissue. The exact depth to which protons penetrate, and at which the Bragg peak occurs, is dependent on the energy of the proton beam. This energy can be very precisely controlled to place the Bragg peak within a tumor or other tissues that are targeted to receive the radiation dose. Because the protons are absorbed at this point, normal tissues beyond the target receive very little or no radiation.

In order to properly focus these dedicated beam lines, complex equipment for beam shaping and collimation as well as target fixation is utilized. Target fixation is achieved by using a light source in which the patient focuses his or her sight. The position of the pupil of the patient's eye is monitored by a video camera. To allow different incident beam angles, the camera and light source can be rotated around the beam axis, thereby varying the radial position of the eye of the patient. The ocular tumor is then treated with small treatment fields with sharp dose gradients created using collimators made out of a high-z metal which are positioned directly in front of the patient.

When using scanned particle beams for treatment of other portions of the body, the collimators of the particle therapy system might be omitted, thereby allowing the space in front of the patient to be used for automated external imaging devices which improve the clinical work flow. However, this set up does not allow the radiation of small fields with sufficient precision for eye treatment. Moreover, the space used by the automated external imaging devices does not allow the installation of target tracking or fixation devices for the treatment of ocular tumors without interfering with the external imaging capabilities.

BRIEF SUMMARY

A system having a unique setup for treating an ocular tumor a light source and a removable cone having a collimator is disclosed. The cone can be easily mounted and un-mounted to a nozzle of either a gantry (rotatable beam outlet) or a more usual fixed beam outlet. The cone includes a cone input and a cone output. The cone input receives radiation for the treatment of the ocular tumor. Typically, this radiation is channeled to the cone input via the previously mentioned nozzle. The collimator is coupled to the cone output and configured to collimate radiation received by the cone output. This collimated radiation is directed to the patient having the ocular tumor.

In order to properly determine that the eye of the patient is positioned properly, a light source connects with the cone. The light source is configured to provide a focusing point of the eye of the patient. A camera is connected with the cone and monitors the position of the eye of the patient. The system may also include at least one x-ray source configured to transmit x-rays through the patient. This x-ray source is paired with a flat panel detector configured to receive x-rays transmitted by the first x-ray source.

Further objects, features and advantages will become readily apparent to persons skilled in the art after a review of the following description, with reference to the drawings and claims that are appended to and form a part of this specification.

DETAILED DESCRIPTION

Figure 1:
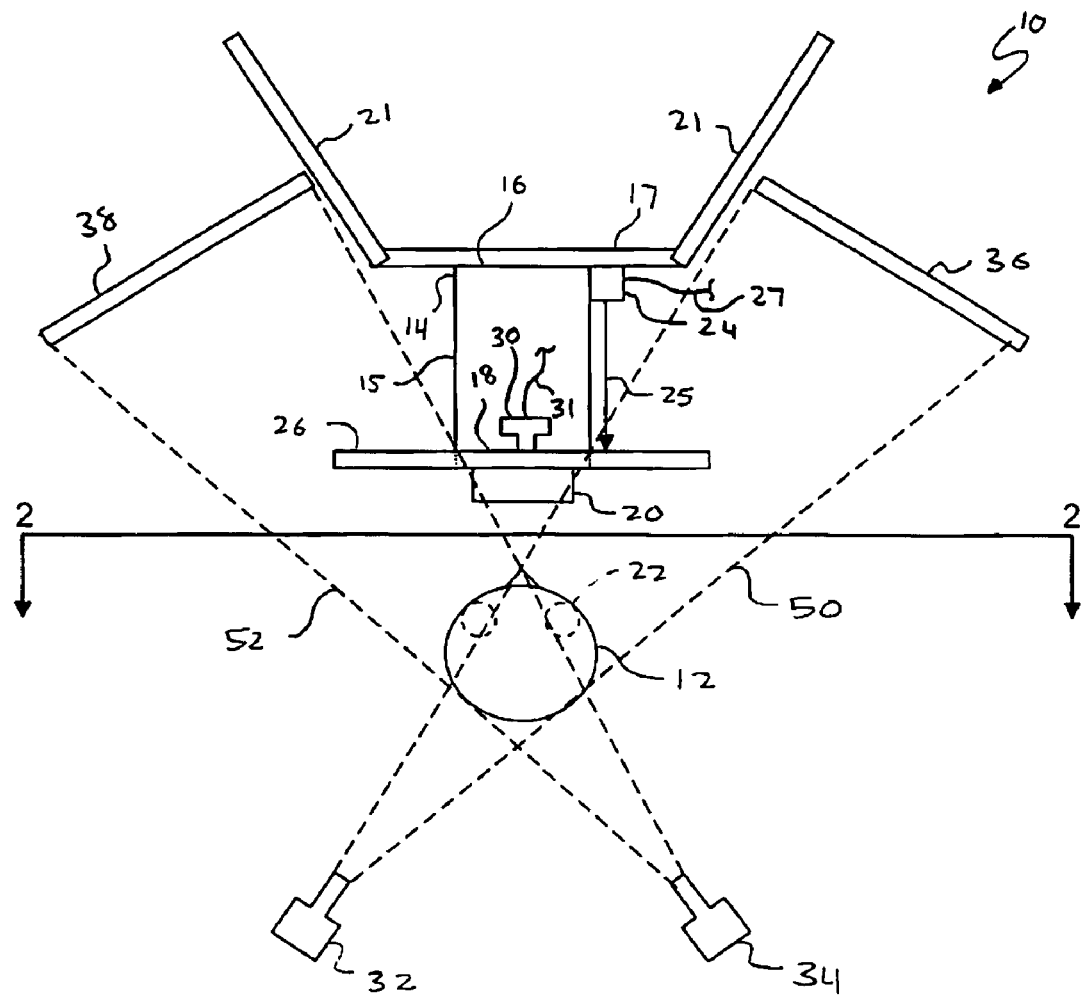
FIG. 1 is a block diagram of one embodiment of a system for treating ocular tumors.
Figure 2:
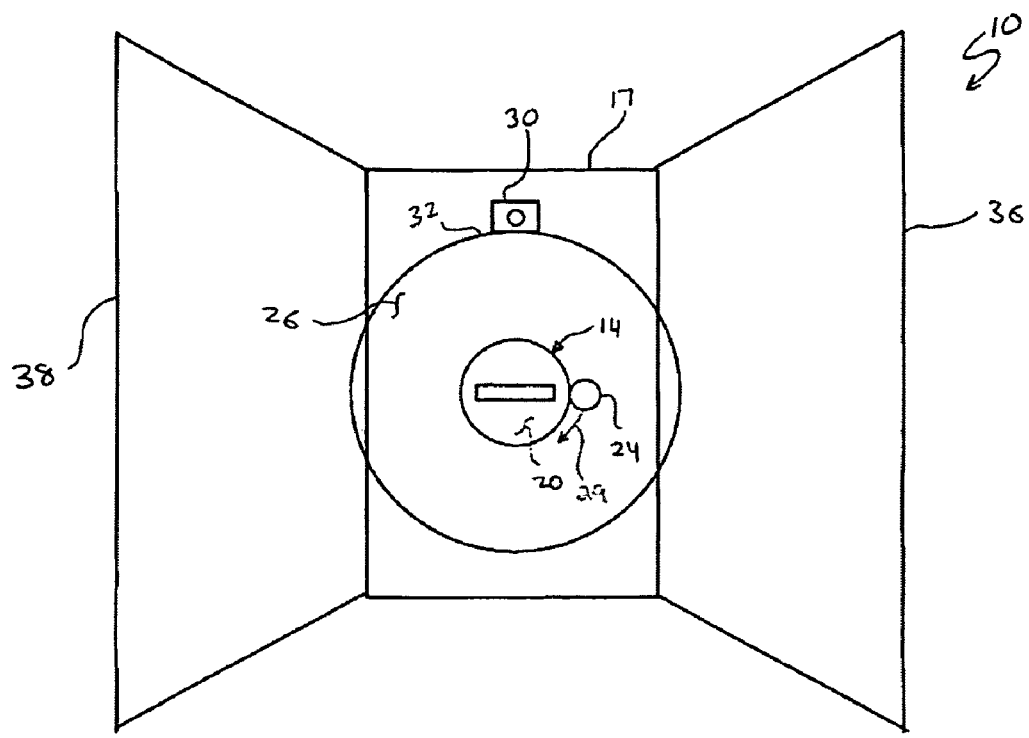
FIG. 2 is a top view of the embodiment shown in FIG. 1.

Referring to FIGS. 1 and 2, a system 10 for treating an ocular tumor or other ocular condition of a patient 12 is shown. The system 10 includes a cone 14 having an elongated body portion 15 with an input 16 and an output 18 located at opposing ends of the body portion 15. The cone 14 may be made of aluminum, plexiglass or any suitable material. As will be described later, the input 16 of the cone 14 receives radiation for treating the ocular tumor of the patient 12. This radiation is transferred from the input 16 of the cone 14 to the output 18 of the cone 14.

The radiation used for treating the ocular tumor of the patient 12 originates from a radiation source (not shown). This radiation is then fed into a treatment nozzle 21. In order to provide this radiation from the treatment nozzle 21, the input 16 of the cone 14 is attached to the treatment nozzle 21. Generally, the input 16 of the cone 14 is a hole. A base plate 17 fixedly attaches to the input 16 of the cone 14. The base plate 17 removably attaches to the treatment nozzle 21. The base plate 17 (and the fixedly attached cone 14) can be readily removed from the treatment nozzle 21, thereby allowing the cone 14 to be easily mounted and un-mounted according to the condition to be treated. For example, the cone 14 may be replaced with another cone having a different collimator size. Additionally, by having the cone 14 capable of being mounted and un-mounted, the cone 14 can be mounted to gantry (rotatable beam outlet) instead of usual fixed beam outlets.

Attached to the output 18 of the cone 14 is a collimator 20. The collimator 20 collimates radiation traveling through the cone 14 in order to focus and direct the radiation to the ocular tumor in the patient 12. More specifically, the collimator 20 is a device that filters a stream of protons so that only those traveling parallel to a specified direction are allowed through. Collimators are used in proton therapy systems because of the sharp gradient at the edges of the irradiation field. The gradient is sharpened by blocking protons outside the collimator close to the patient.

In order to properly treat an ocular tumor, an eye 22 of the patient 12 suffering from the ocular tumor must be properly positioned. A light source 24 capable of drawing the focus of the eye 22 of the patient 12 is coupled to the body portion 15 of the cone 14. This light source 24 is a light emitting diode but may be any light source capable of drawing the focus of the eye 22 of the patient 12. Additionally, the light source 24 may be rotatably attached to the body 15 of the cone 14, allowing the light source 24 to rotate around the body 15 of the cone 14 as indicated by arrow 29 (FIG. 2). This can be accomplished by mounting the light source 24 to ring (not shown) that rotates around the cone 14. By rotating the light source 24 around the body 15 of the cone 14, the eye 22 of the patient can focus in a different direction. More than one light source 24 may be used. The light source 24 may connect at other locations on the cone 14, the nozzle 21 or the projector plate 26. The light source 24 is connected to a multipurpose cable 27 having a plurality of signals including, but not limited to, supply voltage and communication signals. The multipurpose cable 27 is connected to the light source 24 in such a way that it does not obstruct the easy removal of the cone 14. This can be accomplished by using a multipurpose plug (one plug with all the signals) or a sliding contact.

A projector plate 26 is coupled to the body portion 15 of the cone 14 near the output 18 of the cone 14. The projector plate 26 is transparent or semi-transparent and may be made out a transparent polymer. The projector plate 26 is configured to receive light generated by the light source 24 as indicated by arrow 25. The light received by the projector plate 26 from the light source 24 is then displayed on the projector plate so that the eye 12 of the patient 22 can focus on a portion of the projector plate 26 receiving the light from the light source.

In order for an operator of the system 10 to determine the location of the eye 22 of the patient 12, a video camera 30 is provided. The video camera 30 is generally coupled to the body portion 15 of the cone 14, such that the camera 30 can view the eye 22 of the patient 12. Alternatively, as best shown in FIG. 2, the camera 30 may be attached to a perimeter 32 of or other location on the projector plate 26, another location on the cone 14, or a location on the nozzle 21. The video camera 30 is connected to a multipurpose cable 31 having a plurality of signals including, but not limited to, supply voltage and communication signals. The multipurpose cable 31 is connected to the camera 30 in such a way that it does not obstruct the easy removal of the cone 14. This can be accomplished by using a multipurpose plug (one plug with all the signals) or a sliding contact.

Located generally opposing the cone 14 are first and second x-ray sources 32, 34. The first and second x-ray sources 32, 34 are paired with first and second flat panel detectors 36, 38, respectively. The first and second flat panel detectors 36, 38 are generally opposing the x-ray sources 32, 34, respectively and are adjacent to the cone 14 and/or the nozzle 21. When in operation, the first and second x-ray sources 32, 34 output x-ray radiation that travels through the patient 12 to the flat panel detectors 36, 38. By so doing, the operator of the system 10 will be able to visually determine the status of the ocular tumor of the patient 12. Other imaging devices may be used, such as positron emission or ultrasound. While two x-ray sources 32, 34 are shown, one or three or more may be used with a same or different number of detectors 36, 38.

The x-ray sources 32, 34 and detectors 36, 38 are positioned to generate beams extending through the eye 22 without intersecting metallic or radio opaque portions of the particle therapy components. For example and as shown, the beams extend through the polymer plate 26, but do not intersect the nozzle 21 or cone 14. Intersection with same radio opaque components may be provided. The beams from the x-ray sources 32, 34 may be collimated to provide a geometrical relationship with the locations of the x-ray sources 32, 34, the detectors 36, 38 and the eye 22.

Figure 3:
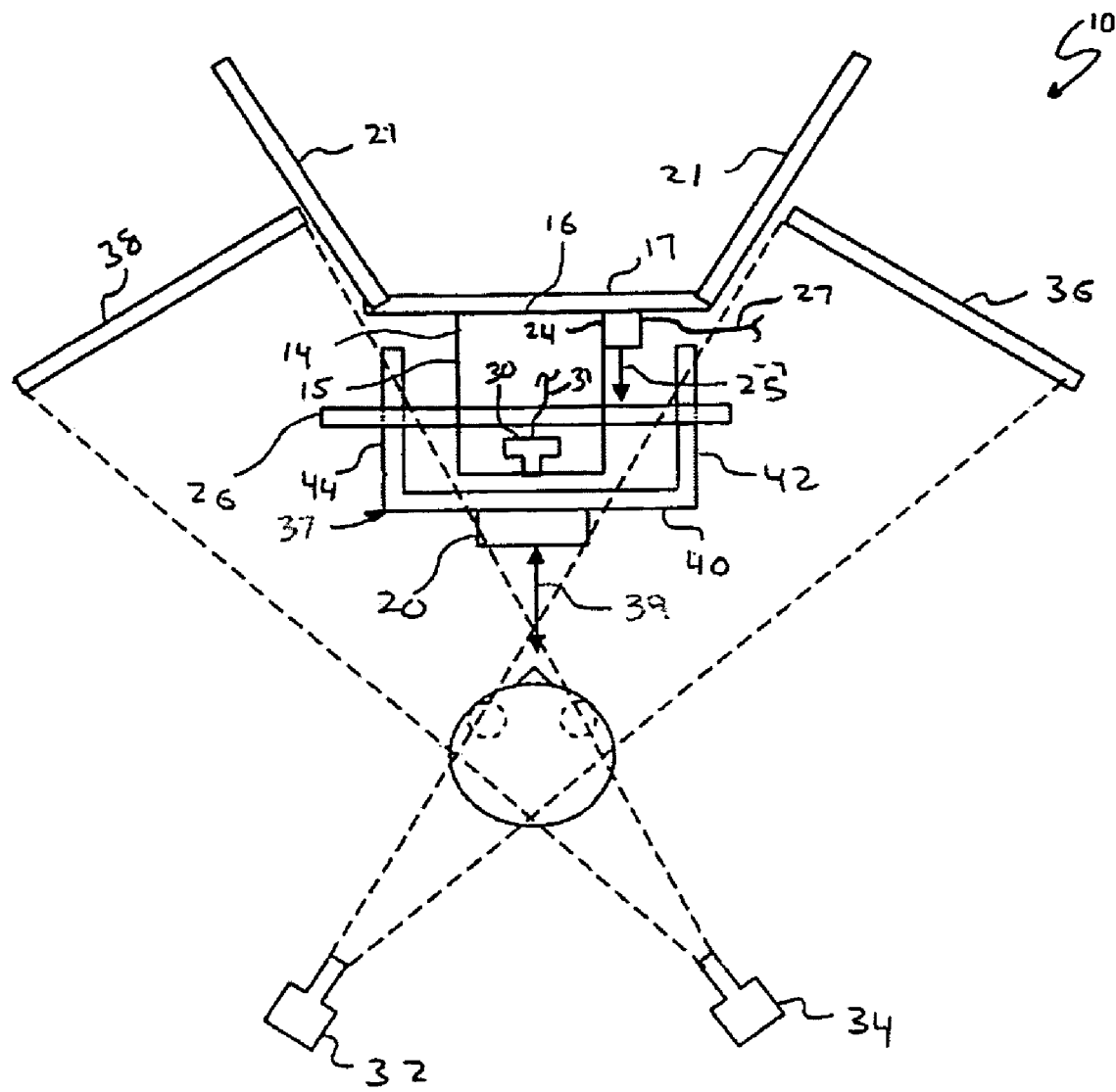
FIG. 3 is a block diagram of another embodiment of a system for treating ocular tumors.

Referring to FIG. 3, another embodiment of the system 10' is shown. This embodiment is similar to the embodiment shown in FIGS. 1 and 2, however, the collimator 20 attaches to a cone extension 37. The cone extension 37 allows the distance 39 between the patient 12 and the collimator 20 to be adjusted. By so doing, the radiation traveling through the cone 14 can be better focused on the ocular tumor of the patient 12. The cone extension 37 may be adjusted by manually operation or may be adjusted with the assistance of a servo motor and screw drive (not shown).

The cone extension 36 may have a front portion 40. a first side portion 42, and/or a second side portion 44. The front portion 40 is coupled to the collimator 20 and generally faces the patient 12. The first and second side portions 42, 44 are attached to front portion 40 and generally extend in a direction away from the patient 12. Generally, this direction is substantially perpendicular to the front portion 40. The optional servo motor (not shown) mechanically engages the first and/or second portions 42, 44, thereby providing automatic adjustment of the cone extension 37. The cone extension 36 is formed from metal or other materials in a beam or slab shapes. Alternatively, plates, cylinders or any suitable shapes may be utilized. The cone extension 37 is oriented to avoid interference with the beams of the x-ray sources 32, 34. Alternatively, some interference is acceptable or at least the intersection portions of the cone extension 37 are substantially x-ray transparent.

Referring again to FIGS. 1 and 2, to operate the system 10, the cone 14 being connected to the base plate 17 is attached to the treatment nozzle 21. By so doing, the cone 14 (and the collimator 20) are capable of receiving radiation provided to the nozzle 21. Thereafter, the patient 12 is located in the general vicinity between the x-ray sources 32, 34 and the collimator 20. More specifically, the patient is located within the line sights 50, 52 of the x-ray sources 32, 34, respectively. Thereafter, radiation is presented to the treatment nozzle 21, which then travels through the cone 14 and the collimator 20 to the patient 12. Before, during or after radiation is presented to the patient 12, the x-ray sources 32, 34 may present x-rays to the patient 12 in order to view the interior of the patient 12. It should be understood that the presentation of radiation to the patient 12 and the presentation of x-rays to the patient may happen over a course of several intervals or may be presented in a single treatment.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

The invention claimed is:

1. A system for treating an ocular tumor, the system comprising:
   a removable cone configured to transfer radiation from a treatment nozzle to a patient, the removable cone having a cone input and a cone output, the cone input being configured to receive the radiation from the treatment nozzle and the cone output being configured to output the radiation to the patient;
   a collimator connected with the cone output, the collimator configured to collimate the radiation received from the cone output;
   a light source connected with the cone and configured to provide a focusing point of an eye of the patient;
   a camera connected with the cone and for monitoring a position of an eye of a patient; and
   a base plate coupled to the input of the cone, the base plate capable of being mounted and un-mounted to the treatment nozzle.

2. The system of claim 1, further comprising:
   a first x-ray source configured to transmit x-rays through the patient; and a first flat panel detector configured to receive x-rays transmitted by the first x-ray source.

3. The system of claim 2, further comprising:
a second x-ray source configured to transmit x-rays through the patient; and
a second flat panel detector configured to receive x-rays transmitted by the second x-ray source.

4. The system of claim 3, further comprising:
the treatment nozzle having a nozzle input and a nozzle output;
the treatment nozzle output being coupled to the base plate and configured to direct radiation received by the treatment nozzle input to the cone input.

5. The system of claim 1, further comprising a transparent projection plate coupled to the cone, the transparent projection plate being configured to display light generated by the light source.

6. The system of claim 5, wherein the transparent projection plate is made of a transparent polymer.

7. The system of claim 1, wherein the light source is a light emitting diode.

8. The system of claim 1, further comprising an adjustable cone extension located between the cone and the collimator, the cone extension being configured to adjust the distance between the collimator and the patient.

9. The system of claim 8, wherein the cone extension further comprises:
a front portion coupled to the collimator, the front portion substantially facing the patient;
a side portion attached to the first portion, the side portion extending away from the patient.

10. The system of claim 8, further comprising a servo motor mechanically coupled to the cone extension for adjusting the distance between the collimator and the patient.

11. The system of claim 1, further comprising a cable connected to the camera, the cable capable of being disconnected from the camera.

12. The system of claim 1, further comprising a cable connected to the light source, the cable capable of being disconnected from the light source.

13. The system of claim 2, further comprising:
the treatment nozzle having a nozzle input and a nozzle output;
the treatment nozzle output being coupled to the base plate and configured to direct radiation received by the treatment nozzle input to the cone input.

14. The system of claim 2, further comprising a transparent projection plate coupled to the cone, the transparent projection plate being configured to display light generated by the light source.

15. The system of claim 14, wherein the transparent projection plate is made of a transparent polymer.

16. The system of claim 2, wherein the light source is a light emitting diode.

17. The system of claim 2, further comprising an adjustable cone extension located between the cone and the collimator, the cone extension being configured to adjust the distance between the collimator and the patient.

18. The system of claim 17, wherein the cone extension further comprises:
a front portion coupled to the collimator, the front portion substantially facing the patient;
a side portion attached to the first portion, the side portion extending away from the patient.

19. The system of claim 17, further comprising a servo motor mechanically coupled to the cone extension for adjusting the distance between the collimator and the patient.

20. The system of claim 2, further comprising a cable connected to the camera, the cable capable of being disconnected from the camera.

21. The system of claim 1, further comprising a cable connected to the light source, the cable capable of being disconnected from the light source.

22. A method for treating an ocular tumor, the method comprising:
attaching a removable cone to a treatment nozzle, the cone having a cone input and a cone output;
locating a patient between the cone and at least one x ray source;
providing a radiation to the treatment nozzle,
transferring the radiation from the treatment nozzle to the patient via the removable cone, wherein radiation emitted by treatment nozzle is inputted into the cone input and is then outputted to the patient from the cone output;
providing x-rays from the at least one x-ray source to the patient.

23. The method of claim 22, wherein the steps of providing a radiation to the treatment nozzle and providing x-rays from the at least one x-ray source to the patient occur simultaneously.

24. The method of claim 22, wherein the steps of providing a radiation to the treatment nozzle and providing x-rays from the at least one x-ray source to the patient occur sequentially.

* * * * *